United States Patent [19]

Nakamura et al.

[11] Patent Number: 5,190,978

[45] Date of Patent: Mar. 2, 1993

[54] CARCINOSTATIC COMPOSITIONS AND METHODS

[75] Inventors: Shingo Nakamura, Joyo; Yoshichika Nishimura, Kyoto; Sensuke Naruse, Tsu; Nobuhiko Miwa, 20-17 Mikkaichimachi, Shobara-shi, Hiroshima-ken, all of Japan

[73] Assignees: Dai-Ichi Kogyo Seiyaku Co. Ltd., Kyoto; Nobuhiko Miwa, Hiroshima, both of Japan

[21] Appl. No.: 589,580

[22] Filed: Sep. 28, 1990

[30] Foreign Application Priority Data

Sep. 29, 1989 [JP] Japan .................... 1-255674
Sep. 29, 1989 [JP] Japan .................... 1-255675

[51] Int. Cl.$^5$ ........................... A61K 31/045
[52] U.S. Cl. ......................... 514/738; 514/739
[58] Field of Search ............... 514/567, 738, 739

[56] References Cited

U.S. PATENT DOCUMENTS 4,916,160 4/1990 Morita .................... 514/546
4,985,466 1/1991 Deguchi .................. 514/724

FOREIGN PATENT DOCUMENTS 175468 3/1986 European Pat. Off. .

*Primary Examiner*—Frederick E. Waddell
*Assistant Examiner*—T. J. Criares
*Attorney, Agent, or Firm*—Millen, White, Zelano and Branigan

[57] ABSTRACT

Presented are pharmaceutical carcinostatic compositions comprising as active ingredient a diol represented by the formula:

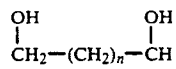

wherein n is an integer of 6 to 33; or by the formula:

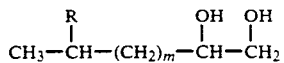

wherein R is hydrogen or $C_1$ to $C_5$ alkyl and m is an integer of 3 to 21; and methods of treatment of cancer of animals with a diol represented by the above formulas. The compositions and the methods are useful for cancer treatment without causing side effects.

15 Claims, 6 Drawing Sheets

CARCINOSTATIC COMPOSITIONS AND METHODS

BACKGROUND OF THE INVENTION

This invention relates to novel carcinostatic compositions and methods of cancer chemotherapy.

Several types of carcinostatic agents are known. These include (a) alkylating agents which exhibit the effect by alkylating such biomolecules with indispensable roles as nucleic acids and enzymes, (b) metabolite antagonists which inhibit metabolism of nucleic acids, (c) mitotic poisons which may influence biosynthesis of nucleic acids, (d) carcinostatic antibiotics which exhibit cytocidal activity against the cells in rapid proliferation, (e) carcinostatics derived from plants and (f) carcinostatic hormones.

These carcinostatic agents, however, are not free from side effects, and few of them exhibit fully satisfactory effects. Consequently, novel agents with improved characteristics are needed.

SUMMARY OF THE INVENTION

It is a principal object of the present invention to provide a class of novel carcinostatic compositions suitable for the treatment of cancers of animals. It is another object of the present invention to provide methods of treatment of cancer of animals with the active ingredient of the compositions of the present invention.

Through an intensive investigation for a novel carcinostatic agent which would cause substantially no side effects, the present inventors have discovered that $\alpha,\omega$-diols of the formula (I):

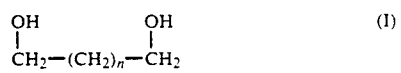

wherein
n is an integer of 6 to 33;
and
$\alpha, \beta$-diols of the formula (II):

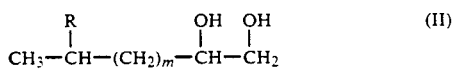

wherein
R is hydrogen or $C_1$ to $C_5$ alkyl; and
m is an integer of 3 to 21; exhibit a remarkable carcinostatic effect on cancer of animals.

Therefore, the present invention provides novel pharmaceutical compositions for chemotherapy of cancer of animals comprising, in admixture with pharmaceutically acceptable carrier, as active ingredient a pharmacologically active amount of a diol represented by the formula (I):

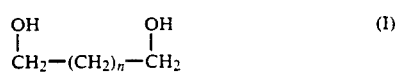

wherein
n is an integer of 6 to 33;
or the formula (II):

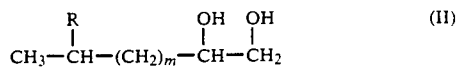

wherein R is hydrogen or $C_1$ to $C_5$ alkyl, and m is an integer of 3 to 21.

In another aspect, the present invention provides a method of treatment of cancer of animals which comprises administering orally or parenterally a pharmacologically effective amount of a diol represented by the formula (I):

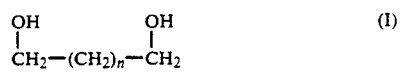

wherein
n is as defined above;
or by the formula (II):

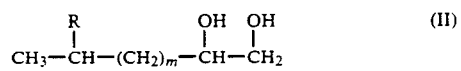

wherein R and m are as defined above.

DETAILED DISCUSSION

Figure 1:
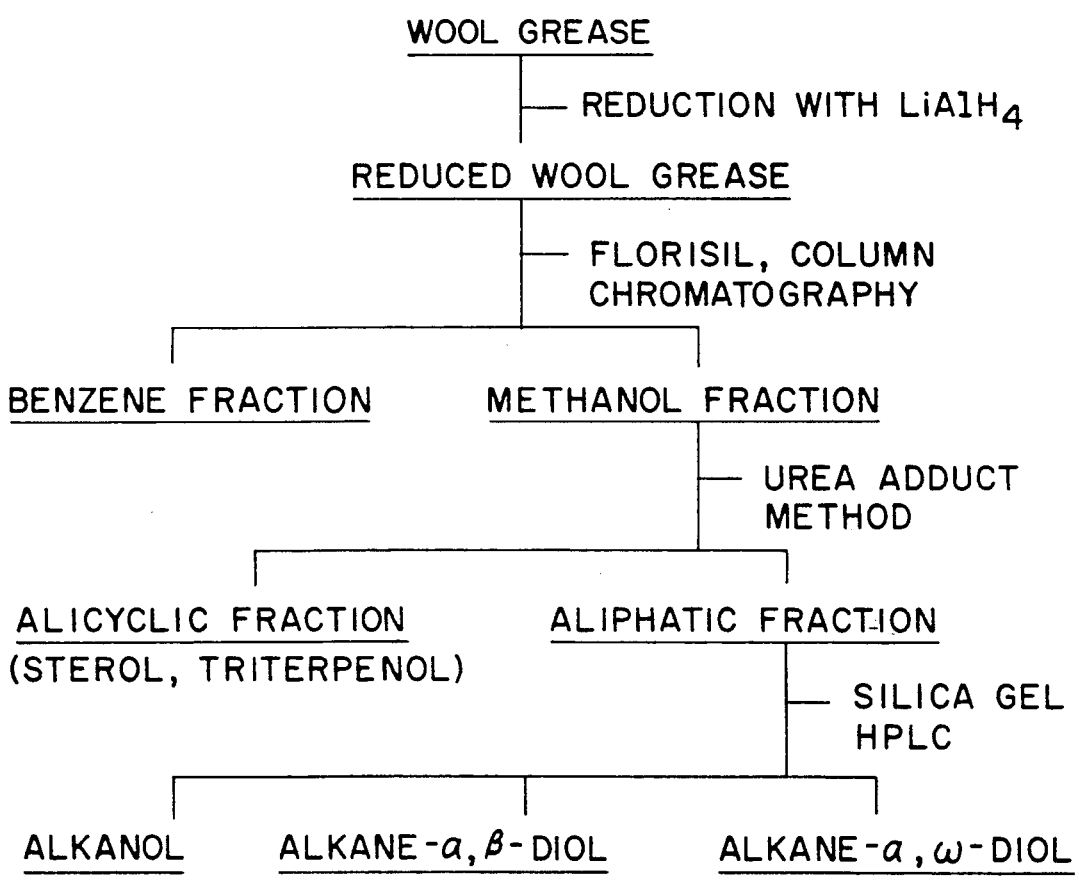
FIG. 1 is a flow chart which illustrates the steps of one method which can be employed for isolating alkane-$\alpha,\beta$- and $\alpha,\omega$-diols from wool grease.

In the formula (I), n is an integer of 6 to 33. More preferably, n is an integer of 12 to 18, and most preferably, n is an integer of 14 to 18.

It has been found that diols of the formula (I) lose carcinostatic activity when n is less than 6 or more than 33. It has also been found that the diols of the formula (I) exhibit a markedly potent carcinostatic activity when n is an integer of 12 to 18.

In the formula (II), R is hydrogen or $C_1$ to $C_5$ alkyl and m is an integer of 3 to 21. More preferably, R is hydrogen or methyl and m is an integer of 12 to 16. Even more preferably, R is hydrogen or methyl and m is an integer of 12 to 14. Most preferably, R is hydrogen when m is 12 and methyl when m is 13.

It has been found that diols of the formula (II) lose carcinostatic activity when m is less than 3 or more than 21. It also has been found that diols of the formula (II) lose carcinostatic activity when R is an alkyl of 6 carbon atoms or more.

A markedly potent carcinostatic activity has been found when R is hydrogen or methyl or when m is an integer of 12 to 16. Among others, 16-methyl-1,2-heptadecanediol of the formula (III):

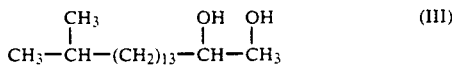

and 1,2-hexadecanediol of the formula (IV);

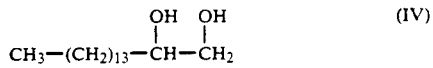

exhibit an especially potent carcinostatic activity.

Examples of diols used in the present invention include 1,16-hexadecanediol, 1,17-heptadecanediol, 1,18-octadecanediol, and 1,19-nonadecanediol, 1,20-eicosanediol corresponding to the α, ω-diols of the formula (I), and 14-methyl-1,2-pentadecanediol, 15-methyl-1,2-hexadecanediol, 16-methyl-1,2-heptadecanediol, 17-methyl-1,2-octadecanediol, 18-methyl-1,2-nonadecanediol, 1,2-pentadecanediol, 1,2-hexadecanediol, 1,2-heptadecanediol, 1,2-octadecanediol and 1,2-nonadecanediol corresponding to the α, β-diols of the formula (II).

A diol of the formula (I) or (II) may be used alone or optionally in mixture with one or more other diols of the formula (I) or (II).

The pharmaceutical compositions of the present invention may be prepared, for example, as follows:

For preparing a pharmaceutical composition of the present invention, for parenteral administration the diol of the formula (I) or (II) may be admixed with water for injection and a surfactant such as a poloxamer, for example Pluronic F-68 (commercial name, ASAHI DENKA KOGYO K.K.), HCO-60 (commercial name, NIKKO CHEMICALS K.K.) and the like, and then dispersed ultrasonically. A type of composition such as liposome suspension or oil-in-water emulsion comprising a diol of the formula (I) or (II) are examples of suitable compositions for parenteral administration. Such compositions may contain preservatives such as methyl p-hydroxybenzoate, stabilizers such as lecithin or linoleic acid, non-aqueous vehicles such as coconut oil and agents for suspension aid such as glucose.

For preparing a pharmaceutical composition of the present invention, for oral administration the diol of the formula (I) or (II) may be made into the form of capsules suitable for intestinal absorption by incorporating, for example, binders such as gelatin, stabilizers such as magnesium stearate, diluent bases such as lactose and disintegrators such as potato starch and by coating the capsules with acetylphthalylcellulose or acrylic acid-methacrylic acid copolymer to form an enteric coating layer.

Granules, sustained-release capsules for implant, a suppository, a nebulizer or a buccal preparation may also suitably be prepared as a pharmaceutical composition of the present invention.

For parenteral application such as intravenous or subcutaneous injection, the active ingredient of the carcinostatic composition of the present invention may be administered at a dose of 10 to 1500 mg/kg/day for adult human, preferably 50 to 400 mg/kg/day.

In the form of oral composition such as capsules, the dose of the active ingredient of the present invention may be 0.2 to 50 g, preferably 1 to 10 g.

The carcinostatic compositions of the present invention are effective in the treatment not only of ascite tumors and leukemia but also of solid tumors which include adenocarcinoma, squamous cell carcinoma, undifferentiated carcinoma and sarcoma in various tissues. The diols of the formula (I) or (II) are effective not only by direct application to the tumor site but also by application to a remote site of tumor-implanted animals. The diols of the formula (I) or (II) are also effective on cultured malignant tumor cells from human, mouse, rat, hamster and so on. It is thus indicated that the carcinostatic compositions of the present invention may have a direct lethal effect on tumor cells without specificity to animal species.

The $LD_{50}$ of the diols represented by the formula (I) or (II) were determined to be 3.1 to 15 g/kg and 5.4 to 18 g/kg, respectively, in subcutaneous injection in rats. No side effects were observed by repeated application of these diols for up to 10 days at a dose of 1 to 2 g/kg.

Thus, the carcinostatic compositions of the present invention has a potent carcinostatic effect without causing any severe side effects, and may be used for chemotherapy of cancer of animals including humans and domestic animals.

The diols of the formula (I) or (II) which are used as active ingredients of the present invention may be produced by decomposing naturally occurring waxes. The naturally occurring waxes include wool wax, spermaceti, beewax, white wax, carnauba wax and the like.

The diols of the formula (I) (a, w-diols) may be prepared as follows (see FIG. 1):

Anhydrous lanolin (wool grease) is first reduced with lithium aluminium hydride. The reduced lanolin thus obtained is then separated into 2 fractions by column chromatography using Florisil (commercial name, FLORISIL, Inc.) as an immobile phase and benzene and methanol as eluants. The methanol fraction is subjected to further fractionation as follows. Alicyclic compounds such as sterols and triterpenols are removed from the methanol eluted fraction utilizing the urea adduct method to isolate aliphatic compounds. This process may be carried out by the following method.

The methanol eluted fraction is added to a saturated urea solution in water, methanol or a water-methanol mixture solvent, and then gradually evaporated at 30° C. to condense the reaction mixture. Formation of urea adducts may be accelerated by dissolving the methanol fraction beforehand in methylethylketone, methylisobutylketone, sec-butyl alcohol or methylene chloride. The residue containing the crystals of the resulting urea adducts is filtered, washed and fractionated into alicyclic compounds and the urea adducts of aliphatic compounds by column chromatography. The urea adducts of aliphatic compounds thus obtained are decomposed by addition of water and the aliphatic compounds are extracted using a separating funnel.

The extracted aliphatic compounds are fractionated by HPLC using silica gel as an immobile phase. Prior to the fractionation, the sample is esterified with p-nitrobenzoyl chloride to allow detection with a UV detector attached to the HPLC.

The eluate is separated according to the peaks detected in HPLC. Each fraction then is subjected to hydrolysis to give each corresponding diol.

The above-mentioned separation method is in accordance with the method described by Satoshi TAKANO, Makoto YAMANAKA, Kikuhiko OKAMOTO and Fumio SAITO (Allergens of lanolin: parts I and II, Part I: Isolation and Identification of the Allergens of Hydrogenated Lanolin, Journal of the Society of Cosmetic Chemists, 34, P.99-116 (1983)).

Figure 2:
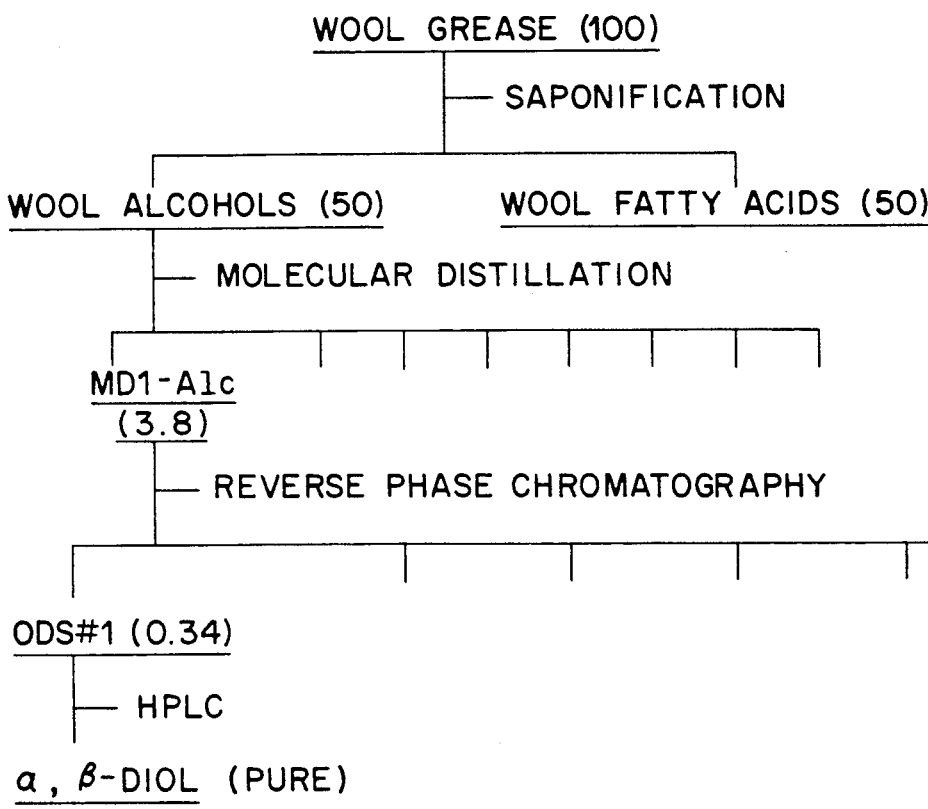
FIG. 2 illustrates an alternative method for isolating an alkane-$\alpha,\beta$-diol from wool grease.

The diols of the formula (II) (α, β-diols) may be prepared not only by the above-mentioned method but also by the following methods. See FIG. 2. Saponification:

A naturally occurring wax such as wool grease is suspended in water containing 1.18 times of NaOH on molar basis, and a saponification reaction is conducted for 3 hours while stirring at 135°±5° C. under pressure in an autoclave. Separation of alcohols from fatty acids:

To the resulting mixed saponification product are added water and methylethylketone (hereinafter referred to as MEK.) The mixture is transferred into a separating funnel and heated to 70° to 75° C. to extract alcohols into MEK. The resulting solution of wool alcohol in MEK is then evaporated in vacuo to give a wool alcohol as solid. Molecular distillation of wool alcohol:

The solid wool alcohol obtained above is subjected to molecular distillation to obtain a fraction with a lower boiling point (temperature; <80° C., pressure; $1 \times 10^{-2}$ Torr.) The fraction is hereinafter referred to as MD1-Alc. Separation of MD1-Alc by reverse phase column chromatography:

MD1-Alc is separated into 6 fractions by reverse phase column chromatography (open column) under the following conditions.

Solid phase: Crushed ODS, pore size 60 Å, particle size 60/200 mesh (commercial name; YMC.GEL, YAMAMURA KAGAKU KENKYUSHO K.K.)

Eluant: $CHCl_3/CH_3OH/H_2O = 5/15/1$ (in volume)

The first fraction, which is the most polar fraction, is hereinafter referred to as ODS#1. Separation of ODS#1 by HPLC; Isolation of each α, β-diol:

According to the following conditions, ODS#1 is separated by HPLC to give the desired compounds.

Column: TSK gel ODS-120 T (commercial name, TOSO K.K.), 21.5 mm I.D.×300 mm

Mobile phase: $CH_3OH/H_2O = 90/10$ (in volume)

Flow rate: 5.0 ml/min

Column temperature: room temperature

The following is an example of the preparation of α, β-diols of the formula (II) which are pharmacologically active compounds of the composition of the present invention. The example is for illustrating purpose only and does not limit the scope of the present invention.

EXAMPLE 200 g of wool alcohol obtained by saponification of wool grease was subjected to molecular distillation to give 15.2 g of MD1-Alc as a fraction with a lower boiling point (temperature; <80° C., pressure; $1 \times 10^{-2}$ Torr.)

The MD1-Alc was separated into 6 fractions by reverse phase column chromatography (open column) using $CHCl_3$—$CH_3OH$—$H_2O$ (5/15/1) mixture as an eluant. The most polar fraction, ODS#1, was obtained in an amount of 1.36 g.

The ODS#1 was further separated by HPLC to isolate each desired compound. Thus obtained were 1,2-hexadecanediol, 16-methyl-1,2-heptadecanediol, 17-methyl-1,2-octadecanediol, 1,2-octadecanediol, 14-methyl-1,2-pentadecanediol, 1,2-tridecanediol. Capillary gas chromalography of each fraction clearly demonstrated that each of these diols were isolated as a pure product.

For determining chemical structures, $^{13}C$-NMR and GC-MS were applied to these isolated compounds and it was comfirmed that these compounds are diols represented by the formula (II).

Figure 3:
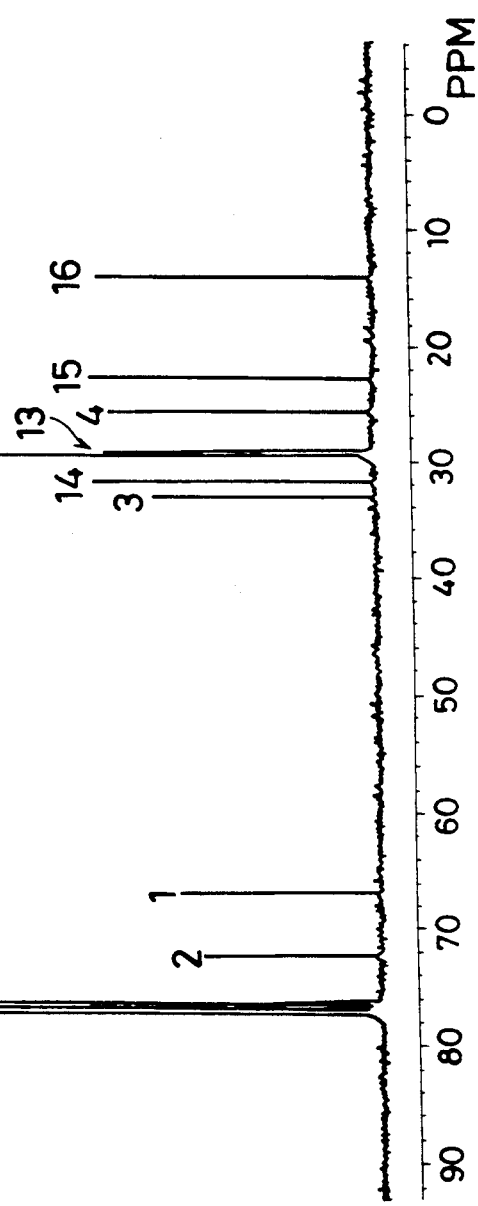
FIG. 3 shows the $^{13}$C-NMR spectrum for 1,2-hexadecanediol.
Figure 4:
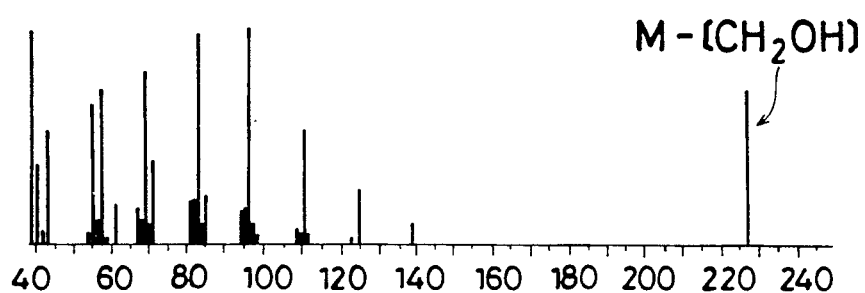
FIGS. 4 and 5 show the GC-MS data of 1,2-hexadecanediol.
Figure 5:
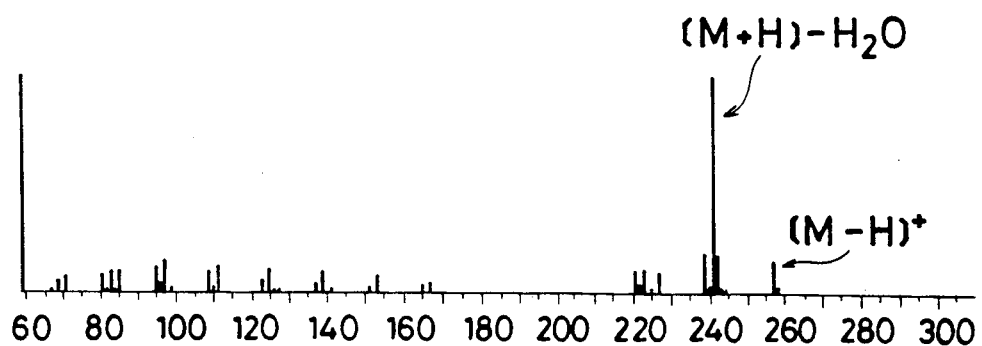
Figure 6:
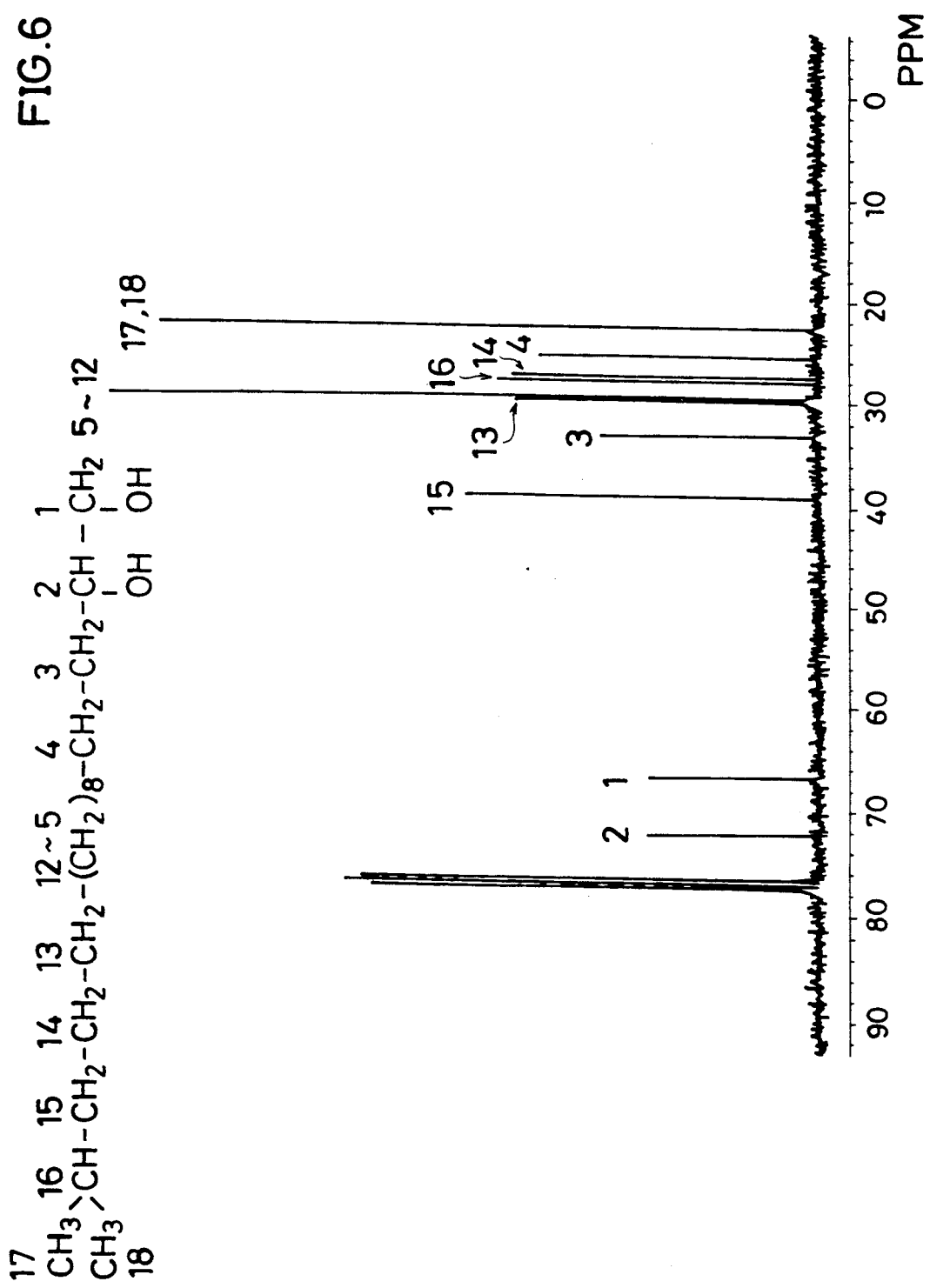
FIG. 6 shows the $^{13}$C-NMR spectrum for 1,2-heptadecanediol.
Figure 7:
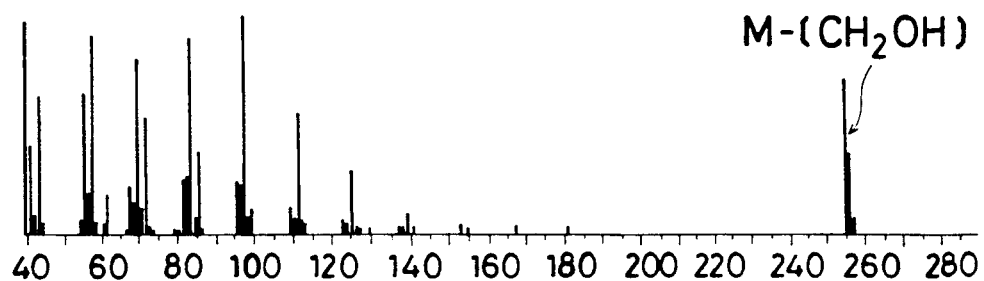
FIGS. 7 and 8 show the GC-MS data of 1,2-heptadecanediol.
Figure 8:
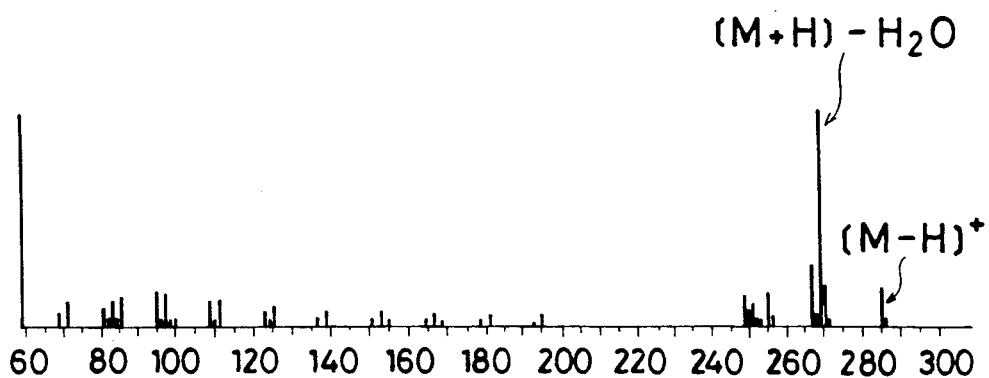

FIG. 3 shows $^{13}C$-NMR spectrum (100.40 MHz, $CDCl_3$, δ ppm) of 1,2-hexadecanediol, and FIG. 4 and FIG. 5 show GC-MS data thereof. FIG. 6 shows $^{13}C$-NMR spectrum (100.40 MHz, $CDCl_3$, δ ppm) of 16-methyl-1,2-heptadecanediol, and FIG. 7 and FIG. 8 show GC-MS data thereof. Data shown in FIG. 4 and FIG. 7 were obtained in mode EI with an ionizing voltage of 70 eV and with the temperature of the ion source of 250° C. Data shown in FIG. 5 and FIG. 8 were obtained in mode CI using isobutane as reacting gas, with an ionizing voltage of 200 eV and with the temperature of the ion source of 250° C.

The diols of the formulas (I) and (II) isolated hereinabove were tested in vivo and in vitro for carcinostatic activity.

TEST 1

5-week old ddY mice were used in the test. The animals were intraperitoneally inoculated with $10^6$ Ehrlich's ascite carcinoma cells.

24 Hours later, 50 mg/ml suspension of a test compound in 0.25 w/w % Pluronic F68 in physiological saline was intraperitoneally injected to 10 animals/group at a dose of 10 mg/kg/day for 5 days.

The mean survival time after inoculation was 14.0 days for the animals receiving the carrier solution without a test compound. On the other hand, the mean survival time of the animals receiving the test compounds was 55.0 days or more for 1,18-octadecanediol, 48.5 days for 1,20-eicosanediol, 52.0 days or more for a 1:1 mixture of these two compounds, 60 days or more for 16-methyl-1,2-heptadecanediol, 56.5 days for 1,2-hexadecanediol and 60 days or more for a 1:1 mixture of the last two compounds. The effects of the test compounds on prolonging survival time of animals were found to be statistically significant.

TEST 2

6-week old $F_1$ mongrel mice of C57BL/6 and DBA/2 were used. The animals were inoculated under back skin with $10^6$ adenocarcinoma 755 cells. 24 Hours later, 50 mg/ml suspension of a test compound in 0.25 w/w % HCO-60 in physiological saline was subcutaneously injected to 8 animals/group at a dose of 10 mg/kg/day for 5 days. The animals were sacrificed 10 days after the inoculation of adenocarcinoma 755 cells, and the tumor was excised.

The mean tumor weight of the control animals was 6.5 g. On the other hand, it was 2.5 g, 1.8 g and 1.5 g for the animals receiving 1,16-hexadecanediol, 17-methyl-1,2-octadecanediol and 1,2-octadecanediol, respectively. The tumor growth suppressing effects of these test compounds were found to be statistically significant.

TEST 3

14-methyl-1,2-pentadecanediol and 1,2-tridecanediol were tested for tumor growth suppressing effect on three different tumor cell strains i.e. Ehrlich's ascites carcinoma cells, human lung carinoma A549 cells and mouse neuroblastoma NAs-1 cells. The results shown below demonstrate the effectiveness of the test compound on these tumor cells.

These diols suppressed the colony formation rate of human lung carcinoma A549 cells to $2.0 \times 10^{-3}$ and $3.5 \times 10^{-3}$, respectively, by 6-hour treatment at 10 μM.

These diols suppressed also the growth of Ehrlich's ascites carcinoma cells to $5.0 \times 10^{-3}$ and $1.0 \times 10^{-2}$, respectively, by 5-day treatment at 10 μM.

The growth of mouse neuroblastoma NAs-1 cells was suppressed to $8.0 \times 10^{-3}$ and $6.1 \times 10^{-3}$, respectively, by these diols.

What is claimed is:

1. A method of treatment for suppressing the growth of a tumor in an animal having a tumor which is susceptible to such treatment which comprises administering thereto orally or parenterally a pharmacologically effective amount of a diol represented by the formula (I):

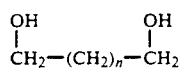

wherein
n is an integer of 6 to 33;
or by the formula (II):

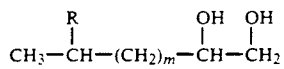

wherein R is a hydrogen of $C_1$ to $C_5$ alkyl and m is an integer of 3 to 21.

2. A method of claim 1 wherein the diol is represented by the formula (I):

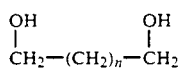

wherein n is an integer of from 12 to 18.

3. A method of claim 1 wherein the diol is represented by the formula (II):

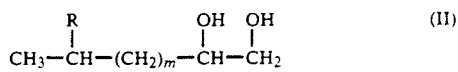

wherein R is hydrogen or methyl and m is an integer of from 12 to 16.

4. A method of claim 2 wherein n is an integer of from 14 to 18.

5. A method of claim 3 wherein R is hydrogen or methyl and m is an integer of from 12 to 14.

6. A method of claim 3 wherein m is 12 or 13, and R is hydrogen when m is 12 and methyl when m is 13.

7. A method of claim 2, wherein the administration is parenteral in the form of an aqueous suspension or emulsion containing a poloxamer surfactant.

8. A method of claim 3, wherein the administration is parenteral in the form of an aqueous suspension or emulsion containing a poloxamer surfactant.

9. A method of claim 2, wherein the administration is parenteral in the form of an aqueous suspension of liposomes or oil-in-water emulsion.

10. A method of claim 3, wherein the administration is parenteral in the form of an aqueous suspension or liposomes or oil-in-water emulsion.

11. A method of claim 2, wherein administration is oral in the form of capsules.

12. A method of claim 3, wherein administration is oral in the form of capsules.

13. A method of claim 1, wherein administration is oral.

14. A method of claim 1, wherein administration is parenteral at a dose of 50 to 40 mg/kg/day.

15. A method of claim 1, wherein the administration is oral at a dose of 1 to 10 g.

* * * * *